United States Patent [19]

Krapiva

[11] Patent Number: 5,645,597
[45] Date of Patent: Jul. 8, 1997

[54] DISC REPLACEMENT METHOD AND APPARATUS

[76] Inventor: Pavel I. Krapiva, 10008 Edward Ave., Bethesda, Md. 20814

[21] Appl. No.: 580,826

[22] Filed: Dec. 29, 1995

[51] Int. Cl.$^6$ .................................................. A61F 2/44
[52] U.S. Cl. ........................... 623/17; 606/61; 128/898
[58] Field of Search .......................... 623/11, 12, 16, 623/17, 18, 66; 606/61; 128/898

[56] References Cited

U.S. PATENT DOCUMENTS

| | | | |
|---|---|---|---|
| 3,875,595 | 4/1975 | Froning | 623/17 |
| 4,545,374 | 10/1985 | Jacobson | 128/303 R |
| 4,772,287 | 9/1988 | Ray et al. | 623/17 |
| 4,863,477 | 9/1989 | Monson | 623/17 |
| 4,911,718 | 3/1990 | Lee et al. | 623/17 |
| 4,932,969 | 6/1990 | Frey et al. | 623/17 |
| 5,002,576 | 3/1991 | Fuhrmann et al. | 623/17 |
| 5,035,716 | 7/1991 | Downey | 623/17 |
| 5,047,055 | 9/1991 | Bao et al. | 623/17 |
| 5,108,438 | 4/1992 | Stone | 623/17 |
| 5,171,280 | 12/1992 | Baumgartner | 623/17 |
| 5,192,326 | 3/1993 | Bao et al. | 623/17 |
| 5,192,327 | 3/1993 | Brantigan | 623/17 |
| 5,514,180 | 5/1996 | Heggeness et al. | 623/17 |

FOREIGN PATENT DOCUMENTS

| | | | |
|---|---|---|---|
| 0621020 | 10/1994 | European Pat. Off. | 623/17 |
| 2639823 | 6/1990 | France | 623/17 |
| 3741493 | 6/1989 | Germany | 623/17 |

*Primary Examiner*—Debra S. Brittingham
*Attorney, Agent, or Firm*—Aquilino & Welsh

[57] ABSTRACT

A method for replacing a nucleus pulposus of an intervertebral disc. The method is achieved by removing the nucleus pulposus from the intervertebral disc to create a space defined by an inner wall of a annulus fibrosis. A flexible prosthetic disc is then inserted within the space formerly occupied by the nucleus pulposus and the prosthetic disc is subsequently filled with a gel.

6 Claims, 3 Drawing Sheets

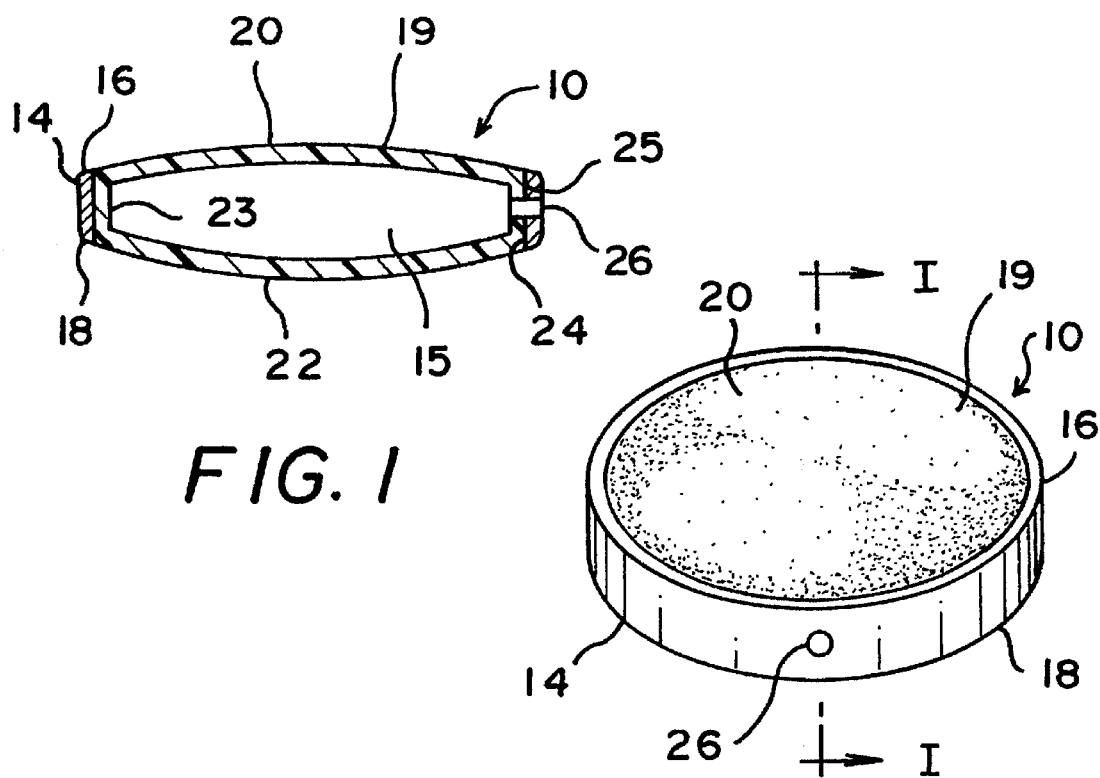
FIG. 1
FIG. 2
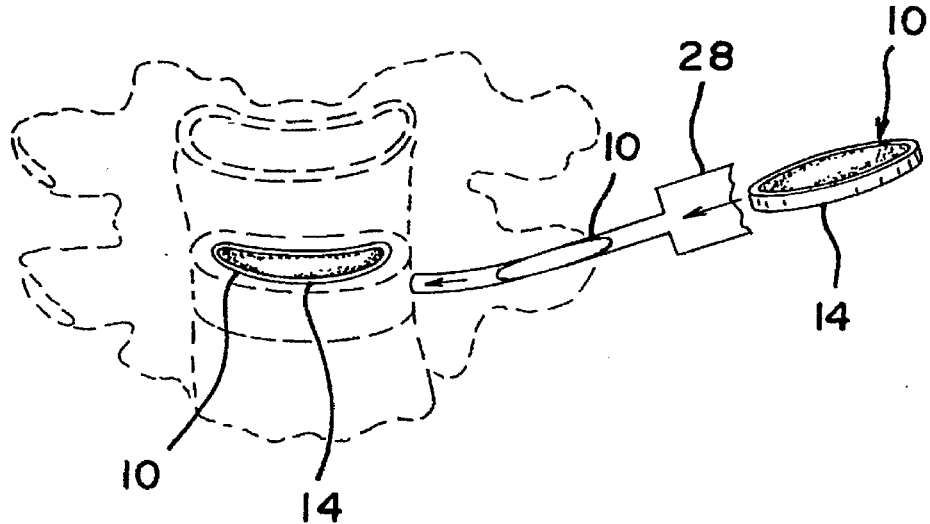
FIG. 3

DISC REPLACEMENT METHOD AND APPARATUS

BACKGROUND OF THE INVENTION

1. Field of the Invention

This invention relates to a method for replacing an intervertebral disc nucleus. More particularly, the invention relates to a prosthetic device used to position a gel material within the disc nucleus.

2. Description of the Prior Art

The intervertebral disc is a complex joint composed of three component structures: the nucleus pulposus, the annulus fibrosis and the vertebral end-plate. These components work to absorb the shock, stress and motion imparted to the human vertebrae.

The nucleus pulposus occupies 25–40% of the total disc cross-sectional area. It is composed mainly of mucoid material primarily containing proteoglycans with a small amount of collagen. The nucleus pulposus is a loose, amorphous hydrogel having the capacity to bind water. In fact, the nucleus pulposus usually contains 70–90 percent water by weight.

The annulus fibrosis maintains the nucleus pulposus within the center of an intervertebral disc. It is composed of highly structured collagen fibers embedded in an amorphous based substance, also composed of water and proteoglycans.

The two vertebral end-plates are composed of hyalin cartilage, which is a clear "glassy" tissue. The vertebral end-plates separate the disc from adjacent vertebral bodies. This layer acts as a transition zone between the hard, bony vertebral bodies and the soft disc. Because the intervertebral disc is a vascular, most nutrients needed by the disc for metabolism are transported to the disc by diffusion through the end plate area.

The intervertebral joint exhibits both elastic and viscus behavior. Hence, during the application of a load to the disc, there is an immediate distortion or deformation of the disc, often referred to as "instantaneous deformation". Because the natural nucleus of the disc is in the form of a loose hydrogel, which can be deformed easily, the extent of deformation of the disc is largely dependant on the extensibility of the annulus fibrosis. Without the constraint from the annulus fibrosis, bulging of the nucleus pulposus would increase considerably.

Because of the constant pressures applied to the intervertebral disc, the disc often degenerates and may ultimately need medical attention. Specifically, the permanent degenerative processes lead to an impairment in blood supply of the disc tissue with subsequent degeneration, dehydration and loss of elastic properties. There are currently three types of treatment used for treating lower back pain caused by injured or degenerated discs: conservative care, laminectomy and fusion. Each of these treatments has its advantages and limitations. The vast majority of patients with lower back pain, especially those with first-time episodes of back pain, will get better with conservative care treatment.

However, it is not necessarily true that conservative care is the most efficient and economical way to solve the lower back pain problem. Laminectomy usually gives excellent short-term results in relieving the clinical symptoms by removing the herniated disc material (usually the nucleus), which is causing the lower back pain either by compressing the spinal nerve or by chemical irritation. However, a laminectomy is not desirable from a bio-mechanical point of view. In the healthy disc, the nucleus takes most of the compressional loading. However, this load is distributed more into the annulus fibrosis ring when the disc degenerates, causing tearing and delimitation. Removal of the nucleus pulposus in a laminectomy causes the load to be distributed further into the annulus fibrosis ring, which narrows the disc spaces. Fusion generally does a good job in eliminating symptoms and stabilizing the joint. However, because the motion of the fused segment is restricted, fusion increases the range of motion of the adjoining vertebral disc. Possibly enhancing the degenerative process.

In view of the short-comings of the prior back treatments, a method and apparatus for treating intervertebral disc problems is needed. The present invention provides such a method and apparatus.

SUMMARY OF THE INVENTION

It is, therefore, an object of the present invention to provide a method for replacing the nucleus pulposus of an intervertebral disc. The method is achieved by removing the nucleus pulposus from the intervertebral disc to create a space defined by the inner wall of the annulus fibrosis. A flexible prosthetic disc is then inserted within the space formerly occupied by the nucleus pulposus and the prosthetic disc is subsequently filled with a gel.

Additionally it is an object of the present invention to provide an apparatus for replacing the nucleus pulposus within an intervertebral disc. The apparatus includes a prosthetic disc including a flexible ring having an upper edge and a lower edge, wherein an upper membrane is secured to the upper edge and a lower membrane is secured to the lower edge to define a cylindrical space. The prosthetic disc is sized to be positioned within the space occupied by the nucleus pulposus. The apparatus further includes means for facilitating the introduction of a gel within the cylindrical space.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a cross sectional view of a prosthetic disc along I—I of FIG. 2.

FIG. 2 is a perspective view of the prosthetic disc.

FIG. 3 is an internal view showing the insertion of the prosthetic disc shown in FIGS. 1 and 2 within the nucleus pulposus.

DESCRIPTION OF THE PREFERRED EMBODIMENTS

Figure 4:
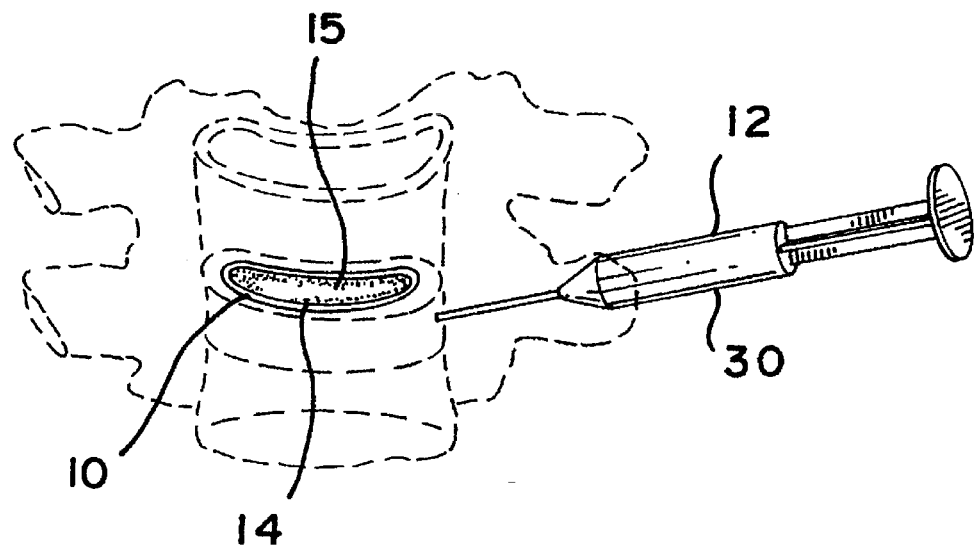
FIG. 4 is an internal view showing the insertion of gel into the prosthetic disc shown in FIGS. 1 and 2.

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

A method and apparatus for replacing the nucleus pulposus is provided. The method is achieved by positioning a flexible prosthetic disc 10 within the space defining the nucleus pulposus and subsequently filling the spaced defined by the prosthetic disc 10 with a gel 12. The present method and apparatus provide a convenient, reliable, and safe method for replacing the nucleus pulposus of an individual who has suffered a back injury.

As shown in FIG. 1, the prosthetic disc 10 includes a flexible ring 14 having an upper edge 16 and a lower edge 18. The flexible ring 14 defines a cylindrical space 15 sized to fit within the space occupied by the nucleus pulposus. The flexible ring 14 is constructed from an elastic metal or plastic thin-walled ring. The ring should be constructed such that it can initially be squeezed and passed via a narrow laparoscopic tube to a desired sight, but will regain its round shape once properly positioned within the prepared nucleus pulposus space. The flexible ring should be constructed from a biologically inert material to prevent inflammatory or immune response reactions. The exact dimensions of the ring 14 will vary with the application of the ring. Specifically, a wide range of sizes will be required depending upon the level of the injured disc, that is, cervical v. lumbar. It should be understood that the exact materials and dimensions of the prosthetic disc can be varied without departing from the spirit of the present invention.

The cylindrical space 15 created by the flexible ring 14 is contained by a capsule shaped membrane 19 secured within the cylindrical space 15 defined by the flexible ring. The capsule shaped membrane 19 includes an upper membrane 20 secured to the upper edge 16 of the flexible ring 14 and a lower membrane 22 secured to the bottom edge 18 of the flexible ring 14. The upper membrane 20 and lower membrane 22 are connected by an annular ring 23 to complete the capsule shaped membrane 19. The capsule shaped membrane 19 is preferably constructed from elastic, biologically inert materials such a teflon or silicon, although other materials could be used without departing from the spirit of the present invention. The materials chosen should aid in the prevention of inflammatory or immune response reactions. The capsule shaped membrane 19 may be secure to the flexible ring in a variety of conventional manners. According to the preferred embodiment, the inner surface 24 of the flexible ring 14 is bonded to the external surface 25 of the annular ring 23 of the capsule shaped membrane 19. Although one embodiment for the construction of the prosthetic disc is disclosed in FIGS. 1 and 2, the disc could be constructed in a wide variety of ways without departing from the spirit of the present invention.

Figure 5:
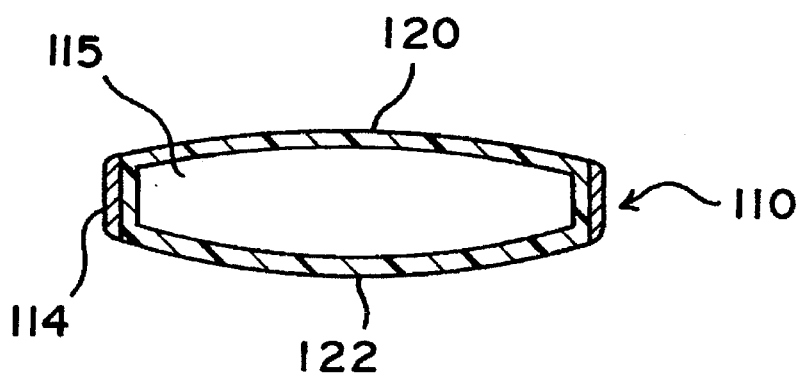
FIG. 5 is a cross sectional view of an alternate prosthetic disc.

According to one embodiment of the present invention, shown in FIGS. 1 and 2, the prosthetic disc 10 has a hole 26 along its circumference permitting the introduction of the gel 12. The hole 26 passes through the flexible ring 14 and the annular ring 23 of the capsule shaped membrane 19. Another embodiment of the prosthetic disc 110 is shown in FIG. 5. This embodiment is constructed in the same manner as the prosthetic disc shown in FIGS. 1 and 2, however, this prosthetic disc 110 is solid around its entire circumference. As will be discussed in more detail below, the gel 12 is introduced into the embodiment of FIG. 5 through the upper or lower membrane 120, 122. Therefore, the upper membrane 120 and/or the lower membrane 122 are made of a resealable materials commonly known and used in the field of prosthetic devices. As with the embodiment discussed above, the upper and lower membranes 120, 122 should be constructed from biologically inert materials that will aid in the prevention of inflammatory or immune reactions. The manner for using both rings will now be discussed in more detail.

With reference to FIGS. 3 and 4, the method for performing the present invention with the first embodiment of the prosthetic disc 10 is disclosed. The nucleus pulposus is surgically removed by way of a hole extending through the annulus fibrosis. After the nucleus pulposus has been removed to the extent determined by the attending physician, a hole passing through the annulus fibrosis remains. The hole is used for the introduction of the flexible prosthetic disc 10 and the subsequent introduction of the gel 12. Specifically, an introducer 28 (preferably a laparoscopic tube), housing the prosthetic disc 10, is passed through the annulus fibrosis and into the space formerly occupied by the nucleus pulposus. The prosthetic disc 10 is then forced out of the introducer 28 and into the spaced formerly occupied by the nucleus pulposus. The prosthetic disc 10 then expands to fill the nucleus space; the flexible ring 14 engaging the inner wall of the annulus fibrosis.

The flexible ring 14 is then rotated so that the hole 26 in the prosthetic disc 10 is aligned with the hole in the annulus fibrosis. A syringe 30, containing the gel 12, is passed through the annulus fibrosis and into the space defined by the prosthetic disc 10. The gel 12 is introduced into the space 15 defined by the prosthetic disc 10 until the prosthetic disc 10 is filled to the extent necessary to replace the nucleus pulposus.

Once the prosthetic disc 10 is completely filled with gel 12, the ring 14 is rotated so that the hole 26 in the ring 14 is no longer aligned with the hole in the annulus fibrosis. The resulting replacement permits the flexible ring 14 and the annulus fibrosis to retain the outward forces produced by the gel 12 when downward pressure is applied to the individual's spinal column. In fact, the annulus fibrosis functions in much the same way it did when the nucleus pulposus was still in place; that is, it acts to retain the outward forces applied by the nucleus pulposus, or the gel after the nucleus pulposus has been replaced.

Figure 6:
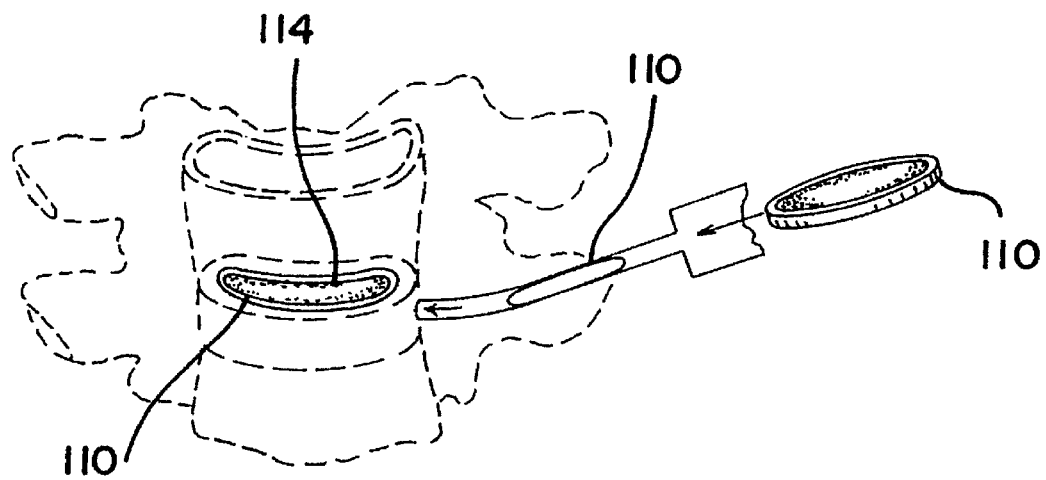
FIG. 6 is an interval view showing the insertion of the prosthetic disc shown in FIG. 5 within the nucleus pulposus.
Figure 7:
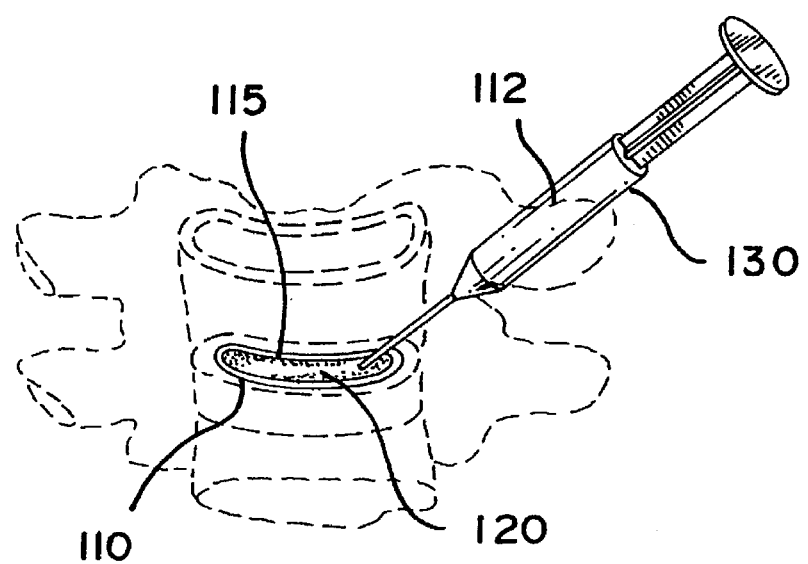
FIG. 7 is an internal view showing the insertion of gel into the prosthetic disc shown in FIG. 5.

With reference to FIGS. 6 and 7, the method for performing the present invention with the second embodiment of the prosthetic disc 110 is disclosed. As with the method previously discussed, the nucleus pulposus is removed and the prosthetic disc is inserted within the space formerly occupied by the nucleus pulposus. The prosthetic disc 110 then expands to fill the nucleus space; the flexible ring 114 engaging the inner wall of the annulus fibrosis.

In contrast to the prior method, it is not necessary to rotate the prosthetic disc 110, since the disc 110 does not include a hole. After the prosthetic disc 110 is properly positioned, a syringe 130, containing the gel 112, is passed through the annulus fibrosis, through the upper or lower membrane 120, 122, and into the space 115 defined by the prosthetic disc 110. The gel 112 is then introduced into the space 115 defined by the prosthetic disc 110 until the prosthetic disc 110 is filled to the extent necessary to replace the nucleus pulposus.

While various preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A method for replacing a nucleus pulposus of an intervertebral disc, comprising the steps of:

removing the nucleus pulposus from the intervertebral disc to create a space defined by an inner wall of an annulus fibrosis, wherein a hole is created in the intervertebral disc upon the removal of the nucleus pulposus;

introducing a flexible prosthetic disc within the space formerly occupied by the nucleus pulposus, wherein the flexible prosthetic disc includes an elastic flexible ring, an upper membrane secured to an upper edge of the flexible ring and a lower membrane secured to a lower edge of the flexible ring to define a cylindrical space, such that the prosthetic disc expands as a result of the flexible ring to fill the space defined by the inner wall of the annulus fibrosis;

positioning a syringe filled with a gel through the hole within the intervertebral disc and into the cylindrical space defined by the prosthetic disc; and filling the prosthetic disc with the gel by forcing the gel from within the syringe.

2. The method according to claim 1, wherein the nucleus pulposus is removed through a hole created in the annulus fibrosis, and the prosthetic disc is introduced through the hole.

3. The method according to claim 2, wherein the prosthetic disc includes an outer wall having a hole through which the gel is introduced.

4. The method according to claim 3, including the further step of aligning the hole within the outer wall of the prosthetic disc with the hole formed in the annulus fibrosis so that the gel may be introduced into the prosthetic disc.

5. The method according to claim 1, wherein the gel is introduced through the upper membrane.

6. The method according to claim 1, wherein the gel is introduced through the lower membrane.

* * * * *